(12) United States Patent
Schaefer et al.

(10) Patent No.: US 9,981,260 B2
(45) Date of Patent: May 29, 2018

(54) COATING METHOD

(71) Applicant: UMICORE AG & CO. KG, Hanau-Wolfgang (DE)

(72) Inventors: Robert Schaefer, Grenzach-Wyhlen (DE); Louis Wall, Wehr-Oeflingen (DE)

(73) Assignee: UMICORE AG & CO.KG, Hanau-Wolfgang (DE)

( * ) Notice: Subject to any disclaimer, the term of this patent is extended or adjusted under 35 U.S.C. 154(b) by 52 days.

(21) Appl. No.: 15/039,450

(22) PCT Filed: Nov. 24, 2014

(86) PCT No.: PCT/EP2014/075420
§ 371 (c)(1),
(2) Date: May 26, 2016

(87) PCT Pub. No.: WO2015/078820
PCT Pub. Date: Jun. 4, 2015

(65) Prior Publication Data
US 2017/0165658 A1   Jun. 15, 2017

(30) Foreign Application Priority Data

Nov. 27, 2013 (EP) .................................. 13194573

(51) Int. Cl.
*B01J 37/02*    (2006.01)
*B01J 35/04*    (2006.01)
*B05D 7/22*     (2006.01)
*F01N 3/022*    (2006.01)
*G01N 25/00*    (2006.01)

(52) U.S. Cl.
CPC ........... *B01J 37/0215* (2013.01); *B01J 35/04* (2013.01); *B05D 7/22* (2013.01); *F01N 3/022* (2013.01); *G01N 25/00* (2013.01)

(58) Field of Classification Search
None
See application file for complete search history.

(56) References Cited

U.S. PATENT DOCUMENTS

| 7,033,837 B1 | 4/2006 | Maier et al. |
| 2001/0024686 A1* | 9/2001 | Kiessling ............. B01J 35/0006 427/235 |

(Continued)

FOREIGN PATENT DOCUMENTS

| DE | 102004040550 A1 | 2/2006 |
| DE | 102004040551 A1 | 2/2006 |

(Continued)

OTHER PUBLICATIONS

International Preliminary Report on Patentability for International Application No. PCT/EP2014/075420 dated May 31, 2016, 4 pages.

(Continued)

*Primary Examiner* — Shamim Ahmed
*Assistant Examiner* — Bradford M Gates
(74) *Attorney, Agent, or Firm* — Smith, Gambrell & Russell, LLP

(57) ABSTRACT

The present invention is concerned with a method of coating a carrier which is used in automotive exhaust catalysis. The carrier is subjected to introducing a coating liquid into its channels. In order to check the height of the coated area a thermographic imaging device is used.

18 Claims, 1 Drawing Sheet

(56) References Cited

U.S. PATENT DOCUMENTS

| | | |
|---|---|---|
| 2003/0044520 A1 | 3/2003 | Kiessling et al. |
| 2008/0107806 A1 | 5/2008 | Mergner et al. |
| 2009/0130294 A1 | 5/2009 | Fehnle et al. |
| 2010/0093527 A1 | 4/2010 | Hasselmann |
| 2012/0177822 A1 | 7/2012 | Hasselmann |
| 2012/0315381 A1 | 12/2012 | Mergner et al. |
| 2012/0321537 A1 | 12/2012 | Mergner et al. |
| 2012/0321842 A1 | 12/2012 | Pfeifer et al. |

FOREIGN PATENT DOCUMENTS

| | | |
|---|---|---|
| DE | 102004051099 A1 | 4/2006 |
| DE | 102005062317 A1 | 7/2007 |
| DE | 102007012928 A1 | 9/2008 |
| DE | 102009037381 A1 | 2/2011 |
| DE | 102010007499 A1 | 8/2011 |
| DE | 102010008700 A1 | 8/2011 |
| EP | 1273344 A1 | 1/2003 |
| WO | 9947260 A1 | 9/1999 |
| WO | 2011098450 A1 | 8/2011 |
| WO | 2011101337 A1 | 8/2011 |

OTHER PUBLICATIONS

Written Opinion for International Application No. PCT/EP2014/075420 dated May 31, 2016, 3 pages.

International Search Report for PCT/EP2014/075420, dated Mar. 4, 2015 in English Language.

\* cited by examiner

COATING METHOD

The present invention is concerned with a method of coating a carrier which is used in automotive exhaust catalysis. The carrier is subjected to introducing a coating liquid into its channels. In order to check the height of the coated area a thermographic imaging device is used.

In the art of coating catalytic exhaust gas converters zone coating of carriers, i.e. carriers like wall flow filters or flow-through honeycombs that are coated only over a part of their length, have become of increased importance.

EP-A1-1273344 discloses a method of zone coating a respective carrier by introducing the coating liquid into the channels from its bottom side and forcing the coating liquid upwards against gravity. For coating over the entire length of the carrier it can be detected when the coating liquid exits the channels through their openings at the top face of the carrier. A sensor, like a capacitive sensor, may be employed to detect when the coating liquid reaches the height of the sensor, such as exiting on the top face or if the level of the coating liquid still is inside the carrier.

WO 2011/101337 A1 describes a method for coating a carrier similar to EP-A1-1273344, but a part of the coating liquid is being guided out of the coating apparatus and into a riser tube that indicates the level of the coating liquid inside the carrier. The level may also be detected automatically by a sensor.

WO 2011/098450 A1 shows a method for coating a carrier similar to EP-A1-1273344, wherein a predetermined volume of the coating liquid is introduced into the carrier by hydraulic means.

None of these methods, however, allow the actual and direct detection of the zone height within the carrier itself. Conventionally, the zone height can be determined by X-Ray measurements similar to security controls at airports. This method, however, is slow, requires a significant effort and huge and complex machinery, thus rendering it unsuitable for routine and process control purposes. Another common method is cutting the carrier parallel to the channels and inspecting the zone lengths visually. This way, however, is expensive because actual sales products will have to be destroyed in significant numbers if this procedure is used for quality control. An in-production control is not feasible having said methods applied.

It was an object of the invention to provide another method for destruction-free determination of coating lengths of coated carriers for the production of automotive exhaust gas converters. In particular the method should be rather easy to be implemented on industrial scale production of automotive exhaust catalysts and be nonetheless robust to survive the harsh production conditions involved. The method should also be applicable with less to no negative impact on working safety.

The problem is solved by a method for the determination of the coating length in a coated carrier for the manufacture of automotive exhaust gas converters, the carriers having a first end face, a second end face, a circumferential surface, a main axis and an axial length L and channels defined by channel walls extending form the first end face to the second end face parallel to the main axis, the method comprising:

Providing a carrier for the manufacture of automotive exhaust gas converters exhibiting a first temperature;
Providing a coating liquid exhibiting a second temperature being different from the first temperature of the carrier;
Aligning the carrier on a suitable means for introducing the coating liquid into the channels of the carrier;
Introducing the coating liquid into the channels of the carrier in such a way that a coating is formed on or in the channel walls, wherein the channels are coated over a portion of their length that is less than the axial length L;
Determining the coated length of the carrier by creating a thermographic image of the coated carrier and assigning sections with different temperatures to coated and not-coated areas of the carrier and determining the coated length of the carrier based on that assignment.

The thermographic image can be obtained by an infrared camera. If a digital infrared camera is used, the image can be processed by an image processing software to determine the coated length (which is also known under the term "zone length" in the art), it is also possible to employ the data for the measured zone length for controlling the process parameters of the coating method in order to control the coating method, thus ensuring the carriers are always provided with the desired coated length. As carriers normal metallic or ceramic carriers of flow-through or wall-flow type are taken.

DETAILED DESCRIPTION OF THE INVENTION

The method of the present invention is performed in a normal way already known to the skilled worker. Preferable coating methods for the production of catalyzed flow-through as well as wall-flow monoliths of metallic or ceramic type can be found in the art (EP1064094A1; DE 102010008700A; DE 102010007499A; DE102009037381A; DE 102007012928A; DE102004051099A; DE102005062317A; DE 102004040551A; DE102004040550A; and literature cited therein). A normal coating station used in such production lines are additionally equipped with an infrared camera used to take the thermographic image. It is preferred if the thermographic image is created by an infrared camera which is able to distinguish between temperatures having a gradient of less than 4, more preferably less than 3 and most preferably less than 2° C.

In a very advantageous embodiment of the present invention the means for creating the thermographic image is arranged at the means for introducing the coating liquid into the channels of the carrier in such a way that the progress of the introduction of the coating liquid into the carrier can be monitored. Having established such kind of process control it is possible to further install an in-production-control process, wherein the coated length determined in the method of the invention is employed to control at least one of the parameters of the introduction of the coating liquid into the carrier, i.e. to create a closed-loop control.

If advantageously a digital infrared camera is used, the image can be processed by an image processing software to determine the coated length (which is also known under the term "zone length" in the art) with preferably minimum error range, e.g. by employing statistical noise reduction algorithms or the like. As already indicated the data collected for the measured zone length can advantageously be used for controlling the process parameters of the coating method in order to control the coating method, thus ensuring the carriers are always provided with the desired coating length. The coating length can be determined without destruction of the coated carriers using the process of the present invention with an error range of less than ±1 cm, preferably less than ±0.5 cm, and most preferably less than ±0.3 cm.

The carriers used for the present invention are normal substrates or support bodies regularly found in automotive exhaust catalysis to carry the catalytically active components along with additional material like binders or high surface area refractory metal oxides used as supporting materials, the latter being introduced into the carrier in form of a suspension called washcoat. If the carriers exhibit porous wall structures it is possible to deposit the washcoat either on the wall or inside the wall or both. This depends on the relation of the pores of the wall and the size of the particles in the washcoat. The skilled reader is equipped with the necessary knowledge to realize both types of coating strategies (see above references). The carriers are advantageously selected from the group of metallic or ceramic flow-through monolith and a metallic or ceramic wall-flow monolith.

In order for the method to work properly the temperature difference of the coating liquid and the carrier, i.e. the first and the second temperature, have to be different. As already stated above the difference is depending on the resolution of the camera used and, thus, the temperature difference of the first and the second temperature should be less than the temperature resolution of the camera. In a very preferred manner the temperature difference of the first and the second temperature is more than 2° C. to get a good differentiation of the end of the coating length inside the carrier. The upper temperature is limited by the technical possibilities dictated by the materials used. For best results, it is required that the difference is at least 3° C., in particular from 3° C. to 30° C., usually in the range of from 4° C. to 15° C., or most preferably from 5° C. to 10° C., taking into account the sensitivity for the digital infrared cameras available today. Smaller differences might be considered when more accurate equipment becomes available. Greater temperature differences are likely to cause problems during processing, either because properties of the coating liquid might change, or providing such a great temperature difference between the first and the second temperature might be difficult to establish because of the energy requirements to heat and/or cool the carrier, the coating liquid or both.

As already indicated if the concept of an in-loop-control of the production of respective coated carriers is realized it makes sense to arrange the means for creating the thermographic image in close proximity to the carrier at the means for introducing the coating liquid into the channels of the carrier. It should be arranged in such a way that the progress of the introduction of the coating liquid into the carrier can be directly monitored. On the other hand the present method can also be used merely for quality control purposes. Regardless of the purpose the present invention provides a method that can be easily installed in large production facilities for automotive exhaust catalysts. The method serves for a further improvement in as much as the end points of a catalytic coating which is less than the total length of the carrier can be monitored rather easily without destruction of the catalyst in question. For zone coated catalysts it is sometimes of absolute necessity that these zones do not merge each other, i.e. one zone may poison the other. Having a high accurate measurement of the zone end may thus lead to the production of superior catalysts.

Figure 1:
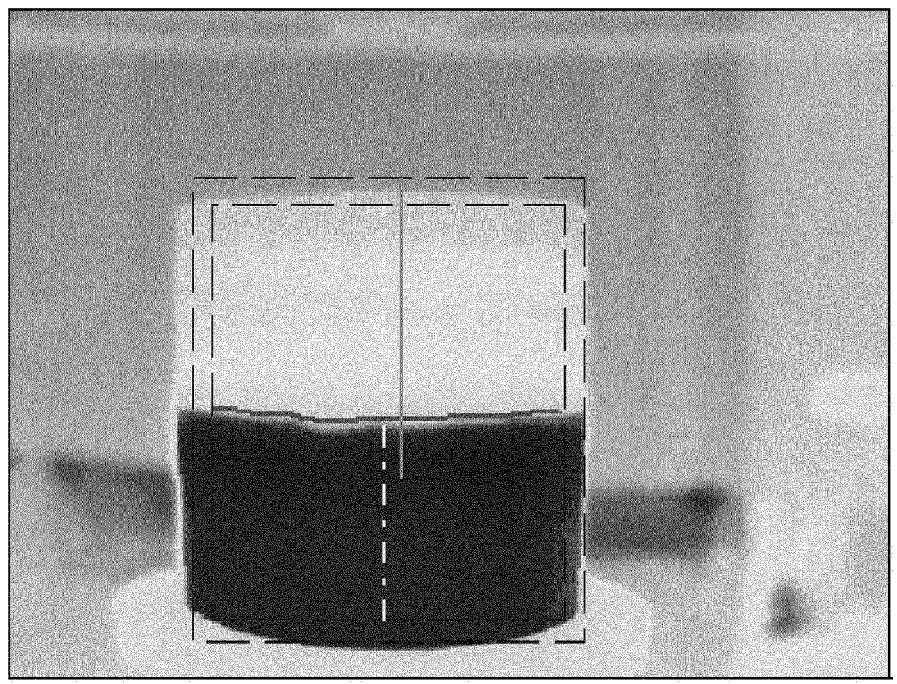
FIG. 1 shows a thermographic image of a carrier after it has been coated with a washcoat of different temperature compared to the carrier. The distinction between carrier and coated zone is clearly visible.
Figure 2:
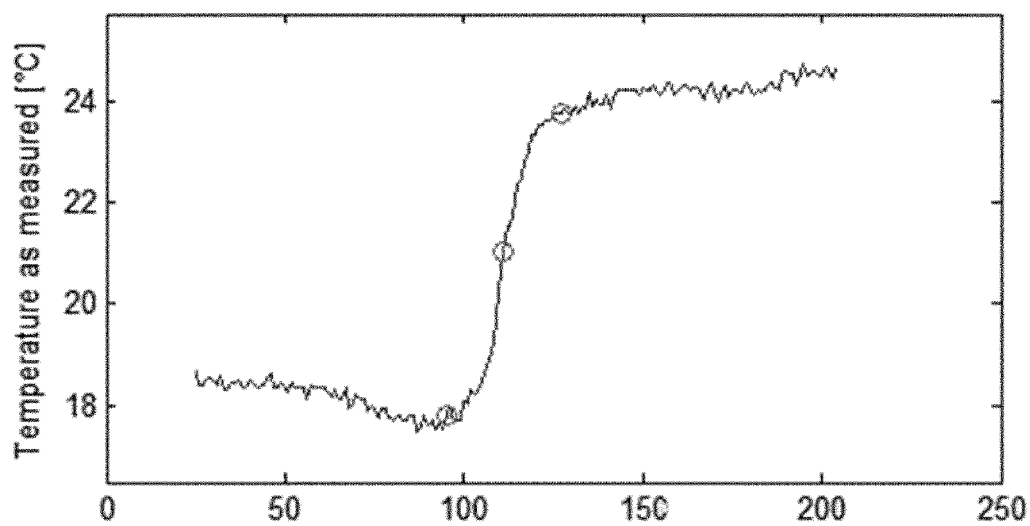
FIG. 2 displays a curve reflecting the temperature measured along the middle axis of the carrier as indicated in FIG. 1 with a grey line. The point of inflection of the curve is taken as the end point of the coated area.

The invention claimed is:

1. A method for the determination of the coating length in a coated carrier for the manufacture of automotive exhaust gas converters, the carrier having a first end face, a second end face, a circumferential surface, a main axis and an axial length L and channels defined by channel walls extending from the first end face to the second end face parallel to the main axis, the method comprising:
   providing the carrier for the manufacture of automotive exhaust gas converters exhibiting a first temperature;
   providing a coating liquid exhibiting a second temperature being different from the first temperature of the carrier;
   aligning the carrier on a suitable means for introducing the coating liquid into the channels of the carrier;
   introducing the coating liquid into the channels of the carrier in such a way that a coating is formed on or in the channel walls, wherein the channels are coated over a portion of their length that is less than the axial length L;
   determining the coated length of the carrier by creating a thermographic image of the coated carrier and assigning sections with different temperatures to coated and not-coated areas of the carrier and determining the coated length of the carrier based on that assignment.

2. A method of claim 1, wherein the thermographic image is created by an infrared camera which is able to distinguish between temperatures having a gradient of less than 4° C.

3. A method of claim 2, wherein determining the coated length of the carrier by creating a thermographic image includes utilization of means for creating the thermographic image which is arranged relative to the means for introducing the coating liquid into the channels of the carrier in such a way that monitoring of the progress of the introduction of the coating liquid into the carrier is enabled.

4. A method of claim 1, wherein determining the coated length of the carrier by creating a thermographic image includes utilization of means for creating the thermographic image which is arranged relative to the means for introducing the coating liquid into the channels of the carrier in such a way that monitoring of the progress of the introduction of the coating liquid into the carrier is enabled.

5. A method of claim 4, further comprising monitoring the progress of the introduction of the coating liquid into the carrier.

6. A method of claim 5, wherein the monitoring of the progress of the introduction of the coating liquid into the carrier comprises presenting an image distinction between non-coated carrier material and coated carrier material on the carrier.

7. A method of claim 5, wherein the monitoring of the progress of the introduction of the coating liquid into the carrier comprises viewing an image distinction between non-coated carrier material and coated carrier material on the carrier.

8. A method of coating a carrier with a liquid coating, comprising:
   employing a coating determination according to claim 1 to control at least one parameter of coating liquid introduction in a closed-loop control to coat the carrier.

9. A method according to claim 1, wherein the carrier is selected from the group of metallic or ceramic flow-through monolith and metallic or ceramic wall-flow monolith.

10. A method according to claim 1, wherein the temperature difference between the first temperature and the second temperature is more than 2° C.

11. A method according to claim 1, wherein the temperature difference between the first temperature and the second temperature is 3° C. to 30° C.

12. A method according to claim 1, wherein the temperature difference between the first temperature and the second temperature is 4° C. to 15° C.

13. A method according to claim 1, wherein the temperature difference between the first temperature and the second temperature is 5° C. to 10° C.

14. A method of claim 1, wherein the thermographic image is created by an infrared camera which is able to distinguish between temperatures having a gradient of less than 3° C.

15. A method of claim 1, wherein the thermographic image is created by an infrared camera which is able to distinguish between temperatures having a gradient of less than 2° C.

16. A method of claim 1, wherein determining the coated length of the carrier is carried out with an error range of less than ±1 cm.

17. A method of claim 1, wherein determining the coated length of the carrier is carried out with an error range of less than ±0.5 cm.

18. A method of claim 1, wherein determining the coated length of the carrier is carried out with an error range of less than ±0.3 cm.

* * * * *